(12) United States Patent
Hussain et al.

(10) Patent No.: US 10,479,762 B1
(45) Date of Patent: Nov. 19, 2019

(54) ZWITTERIONIC SURFACTANT CONTAINING ETHOXYLATE UNITS

(71) Applicant: KING FAHD UNIVERSITY OF PETROLEUM AND MINERALS, Dhahran (SA)

(72) Inventors: Syed M. Shakil Hussain, Dhahran (SA); Muhammad Shahzad Kamal, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

(21) Appl. No.: 16/269,218

(22) Filed: Feb. 6, 2019

(51) Int. Cl.
*C07C 303/32* (2006.01)
*C07C 309/14* (2006.01)
*C09K 8/584* (2006.01)

(52) U.S. Cl.
CPC .......... *C07C 303/32* (2013.01); *C07C 309/14* (2013.01); *C09K 8/584* (2013.01)

(58) Field of Classification Search
CPC ...... C07C 303/32; C07C 309/14; C09K 8/584
See application file for complete search history.

(56) References Cited

U.S. PATENT DOCUMENTS 3,280,179 A 10/1966 Ernst
9,321,985 B1 4/2016 Allen et al.

FOREIGN PATENT DOCUMENTS

| CN | 104556625 B | 2/2016 |
| DE | 281751 A5 | 12/1988 |
| JP | 2270856 A | 11/1990 |

OTHER PUBLICATIONS

Hussain et al. (Synthesis and physicochemical investigation of betaine type polyoxyethylene zwitterionic surfactants containing different ionic headgroups, Journal of Molecular Structure 1178 83-88, Published Oct. 2018) (Year: 2018).*
S.M. Hussain, et al., "Synthesis and performance evaluation of betaine type zwitterionic surfactants containing different degrees of ethoxylation" Journal of Molecular Structure, vol. 1173, Dec. 5, 2018, pp. 1-2 (Abstract Only).
Z. Hui-nian, et al., "Synthesis and properties of ethoxylated sulfobetaine and ethoxylated amine oxide" China Surfactant Detergent & Cosmetics, 2014, pp. 1-2.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

Zwitterionic surfactants having a sulfonate head group and an ethoxylated alkyl tail. A method for synthesizing the surfactants via amidation of an ethoxylated carboxylic acid and an amine catalyzed by a fluoride salt as well as a sulfonation reaction using a sultone is provided.

20 Claims, 7 Drawing Sheets

ZWITTERIONIC SURFACTANT CONTAINING ETHOXYLATE UNITS

STATEMENT REGARDING PRIOR DISCLOSURE BY THE INVENTORS

Aspects of this technology are described in an article "Synthesis and performance evaluation of betaine type zwitterionic surfactants containing different degrees of ethoxylation" published in Journal of Molecular Structure, 2018, Volume 1173, pp 983-989, on Jul. 24, 2018, which is incorporated herein by reference in its entirety.

BACKGROUND OF THE INVENTION

Technical Field

The present disclosure relates to surfactants having ethoxylate units, a sulfonate head group, and an alkyl tail. Additionally, the present disclosure relates to methods for synthesis of these surfactants using an ethoxylated carboxylic acid or salt thereof, an amine, and a sultone.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Crude oil consumption is increasing rapidly with global population growth. Crude oil is one of the world's largest sources of energy that supports 60% of all energy consumption [El-hoshoudy, A., et al., *Hydrophobically associated polymers for wettability alteration and enhanced oil recovery-Article review*. Egyptian Journal of Petroleum, 2016]. Surfactants are widely applied in various oilfield applications including acid diversion [Kam, S., et al., *Experimental study of high-temperature foam for acid diversion*. Journal of Petroleum Science and Engineering, 2007. 58(1-2): p. 138-160], stimulation [Al-Sadat, W., et al., *Rheology of a viscoelastic zwitterionic surfactant used in acid stimulation: Effects of surfactant and electrolyte concentration*. Journal of Petroleum Science and Engineering, 2014. 124: p. 341-349], drilling fluid [Dardir, M., et al., *Preparation and evaluation of cationic bolaform surfactants for water-based drilling fluids*. Egyptian Journal of Petroleum, 2017. 26(1): p. 67-77], well completion [Rodvelt, G., *Vertical Well Construction and Hydraulic Fracturing for CBM Completions*, in *Coal Bed Methane*. 2014, Elsevier. p. 101-135], as well as enhanced oil recovery [Chen, S., et al., *Synthesis and physiochemical performance evaluation of novel sulphobetaine zwitterionic surfactants from lignin for enhanced oil recovery*. Journal of Molecular Liquids, 2018. 249: p. 73-82]. The surfactants are used in oilfields to reduce interfacial tension (IFT) between the aqueous phase and crude oil and promote water-wet behavior of formation rocks.

Surfactants are generally categorized into four classes including anionic, cationic, zwitterionic, and non-ionic surfactants. Recently, zwitterionic-type surfactants have received considerable attention due to their utility in oilfield operations [Zhang, Q.-Q., et al., *Novel zwitterionic surfactant derived from castor oil and its performance evaluation for oil recovery*. Colloids and Surfaces A: Physicochemical and Engineering Aspects, 2015. 483: p. 87-95, incorporated herein by reference in its entirety]. Distinctive properties of zwitterionic surfactants such as high salt tolerance [Kamal, M. S., S. M. Shakil Hussain, and L. T. Fogang, *A Zwitterionic Surfactant Bearing Unsaturated Tail for Enhanced Oil Recovery in High-Temperature High-Salinity Reservoirs*. Journal of Surfactants and Detergents, 2018, incorporated herein by reference in its entirety], excellent biodegradability [Rios, F., et al., *Aerobic biodegradation of amphoteric amine-oxide-based surfactants: Effect of molecular structure, initial surfactant concentration and pH*. Chemosphere, 2017. 171: p. 324-331, incorporated herein by reference in its entirety], high temperature stability [Hussain, S. S., et al., *Synthesis, characterization and surface properties of amidosulfobetaine surfactants bearing odd-number hydrophobic tail*. Journal of Surfactants and Detergents, 2016. 19(2): p. 413-420, incorporated herein by reference in its entirety], and/or good solubility in water [Gerola, A. P., et al., *Micellization and adsorption of zwitterionic surfactants at the air/water interface*. Current Opinion in Colloid & Interface Science, 2017, incorporated herein by reference in its entirety] make them potential materials for various oilfield applications [Martínez-Magadán, J., et al., *Molecular design of high performance zwitterionic liquids for enhanced heavy-oil recovery processes*. Journal of Molecular Graphics and Modelling, 2018. 80: p. 264-271, incorporated herein by reference in its entirety]. Due to a rapidly increasing demand for these surfactants, several synthetic methods have been reported for making different kinds of zwitterionic surfactants [Gerola, A. P., et al., *Zwitterionic Surfactants in Ion Binding and Catalysis*. Current Opinion in Colloid & Interface Science, 2017, incorporated herein by reference in its entirety]. Selection of suitable moieties within the framework of a zwitterionic surfactant plays an important role in its oilfield application [Alves, L., et al., *On the rheology of mixed systems of hydrophobically modified polyacrylate microgels and surfactants: Role of the surfactant architecture*. Journal of colloid and interface science, 2018. 513: p. 489-496, incorporated herein by reference in its entirety]. An improperly chosen surfactant can lead to low recovery, high adsorption onto the reservoir rocks, and/or possible rock dissolution, which may ultimately result in formation damage.

In view of the forgoing, one objective of the present disclosure is to provide a family of zwitterionic surfactants exhibiting good water solubility, high tolerance for salinity, and great thermal stability. Another objective of the present disclosure is to provide methods of preparing these surfactants.

BRIEF SUMMARY OF THE INVENTION

According to a first aspect, the present disclosure relates to a surfactant of formula (I)

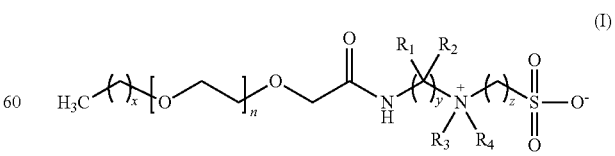

or a solvate thereof, a tautomer thereof, a stereoisomer thereof, or a mixture thereof, wherein (i) $R_1$ and $R_2$ are independently selected from the group consisting of a hydrogen, an optionally substituted alkyl, and an optionally substituted cycloalkyl, (ii) R₃ and R₄ are independently selected from the group consisting of an optionally substituted alkyl, and an optionally substituted cycloalkyl, (iii) n is an integer in a range of 1-15, (iv) x is an integer in a range of 5-21, (v) y is an integer in a range of 2-5, and (vi) z is an integer selected from 3 and 4.

In one embodiment, $R_1$ and $R_2$ are independently selected from the group consisting of a hydrogen and a methyl.

In one embodiment, $R_1$ and $R_2$ are a hydrogen.

In one embodiment, $R_3$ and $R_4$ are independently selected from the group consisting of a methyl, an ethyl, and an isopropyl.

In one embodiment, $R_3$ and $R_4$ are a methyl.

In one embodiment, n is an integer in a range of 2-10.

In one embodiment, x is an integer in a range of 11-13.

In one embodiment, y is 3.

In one embodiment, the surfactant has a formula (II)

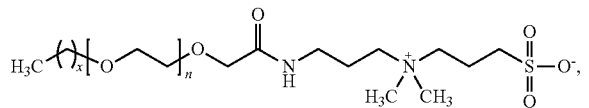

(II)

wherein n is an integer in a range of 1-15, and x is an integer in a range of 11-13.

In one embodiment, the surfactant has a number average molecular weight of 500-1,500 g/mol.

According to a second aspect, the present disclosure relates to a method of synthesizing the surfactant of the first aspect. The method involves mixing a carboxylic acid of formula (III)

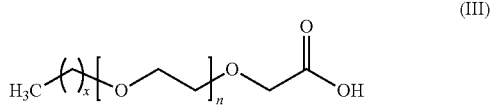

(III)

or a salt thereof, a solvate thereof, or a mixture thereof with an amine of formula (IV)

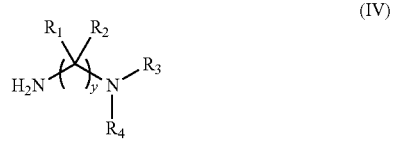

(IV)

or a salt thereof, a solvate thereof, a stereoisomer thereof, or a mixture thereof in the presence of a fluoride salt to form a mixture, heating the mixture to obtain an intermediate, and reacting the intermediate with a sultone of formula (V)

(V)

or a salt thereof, a solvate thereof, or a mixture thereof in a solvent to form the surfactant, wherein (i) $R_1$ and $R_2$ are independently selected from the group consisting of a hydrogen, an optionally substituted alkyl, and an optionally substituted cycloalkyl, (ii) $R_3$ and $R_4$ are independently selected from the group consisting of an optionally substituted alkyl, and an optionally substituted cycloalkyl, (iii) n is an integer in a range of 1-15, (iv) x is an integer in a range of 5-21, (v) y is an integer in a range of 2-5, and (vi) z is an integer selected from 3 and 4.

In one embodiment, the carboxylic acid of formula (III) has a number average molecular weight of 300-800 g/mol.

In one embodiment, the amine of formula of (IV) is 3-(dimethylamino)-1-propylamine.

In one embodiment, the sultone of formula (V) is 1,3-propanesultone.

In one embodiment, a molar ratio of the amine of formula (IV) to the carboxylic acid of formula (III) is in a range of 1:1 to 5:1.

In one embodiment, the mixture further comprises a molecular sieve.

In one embodiment, the molecular sieve comprises aluminum oxide.

In one embodiment, the fluoride salt is sodium fluoride.

In one embodiment, the mixture is heated at a temperature of 100-200° C.

In one embodiment, the reacting is conducted at a temperature of 50-100° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 4 is a FT-IR spectrum of surfactant EASB-1a.

DETAILED DESCRIPTION OF THE EMBODIMENTS

Figure 1:
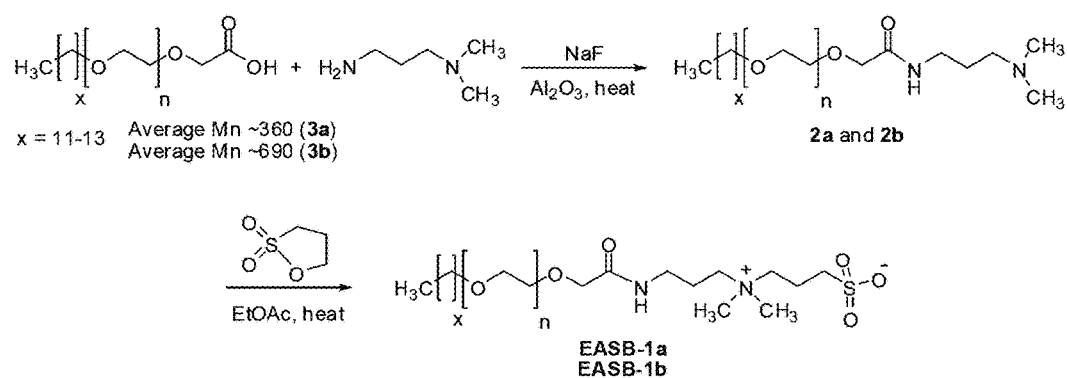
FIG. 1 is a synthetic scheme for preparing surfactants EASB-1a and EASB-1b from a carboxylic acid of formula (III) having a number average molecular weight of about 360 g/mol, and about 690 g/mol, respectively, as well as 3-(dimethylamino)-1-propylamine and 1,3-propanesultone.
Figure 2A:
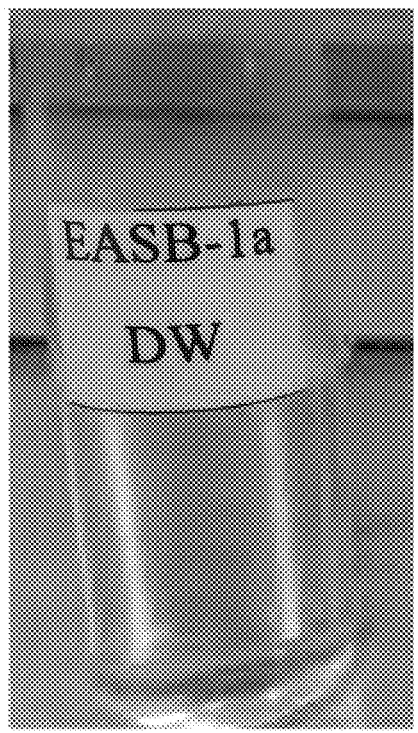
FIG. 2A is a picture showing a solution of surfactant EASB-1a in deionized water (DW).
Figure 2B:
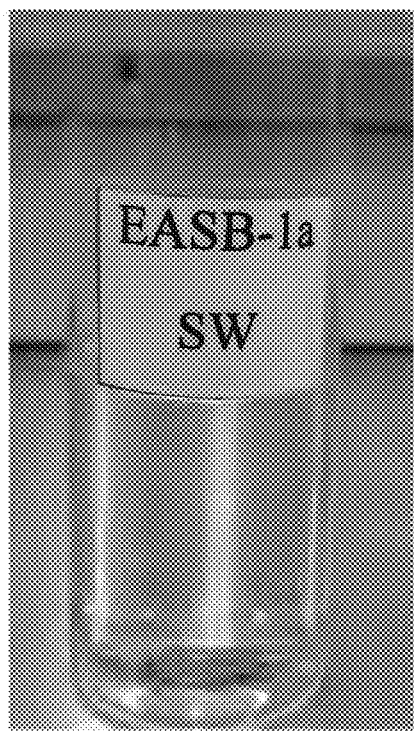
FIG. 2B is a picture showing a solution of surfactant EASB-1a in sea water (SW).
Figure 2C:
FIG. 2C is a picture showing a solution of surfactant EASB-1a in formation water (FW).
Figure 3A:
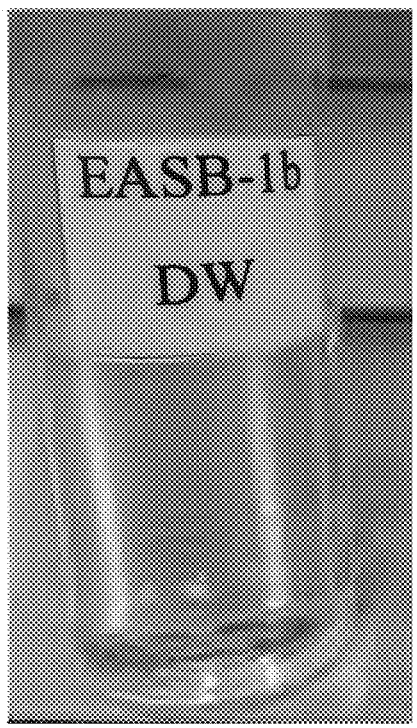
FIG. 3A is a picture showing a solution of surfactant EASB-1b in deionized water (DW).
Figure 3B:
FIG. 3B is a picture showing a solution of surfactant EASB-1b in sea water (SW).
Figure 3C:
FIG. 3C is a picture showing a solution of surfactant EASB-1b in formation water (FW).

Embodiments of the present disclosure will now be described more fully hereinafter with reference to the accompanying drawings, in which some, but not all embodiments of the disclosure are shown.

The present disclosure will be better understood with reference to the following definitions. Unless otherwise specified, "a" or "an" means "one or more". Within the description of this disclosure, where a numerical limit or range is stated, the endpoints are included unless stated otherwise. Also, all values and subranges within a numerical limit or range are specifically included as if explicitly written out.

As used herein, the terms "compound" and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl,—CONHaryl,—CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}$C and $^{14}$C, isotopes of nitrogen include $^{14}$N and $^{15}$N, isotopes of oxygen include $^{16}$O, $^{17}$O and $^{18}$O, and isotopes of sulfur include $^{32-34}$S and $^{36}$S. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a surfactant of formula (I)

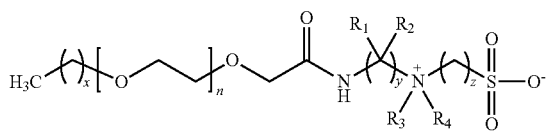

(I)

or a solvate thereof, a tautomer thereof, a stereoisomer thereof, or a mixture thereof. In at least one embodiment, the surfactant is zwitterionic (i.e. amphoteric) having both cationic (e.g. —N$^+$(R$_3$)(R$_4$)—) and anionic (e.g. —SO$_3^-$) groups within the same molecule.

R$_1$ and R$_2$ are independently selected from the group consisting of a hydrogen, an optionally substituted alkyl, and an optionally substituted cycloalkyl. In one or more embodiments, R$_1$ and R$_2$ are independently selected from the group consisting of a hydrogen and a methyl. In a preferred embodiment, R$_1$ and R$_2$ are a hydrogen.

R$_3$ and R$_4$ are independently selected from the group consisting of an optionally substituted alkyl, and an optionally substituted cycloalkyl. In one more embodiments, R$_3$ and R$_4$ are independently selected from the group consisting of a methyl, an ethyl, and an isopropyl. In a preferred embodiment, R$_3$ and R$_4$ are a methyl.

As used herein, the value of x denotes an alkyl chain of —CH$_2$— groups connected to the —CH$_3$ end group of the surfactant of formula (I). In one or more embodiments, x is an integer in a range of 5-21, preferably 7-20, preferably 9-19, preferably 11-18, preferably 13-17, preferably 15-16. Most preferably, x is an integer in a range of 11-13.

As used herein, the value of y denotes an alkyl chain of —C(R$_1$)(R$_2$)— groups of the surfactant of formula (I). In one or more embodiments, y is an integer in a range of 2-5, preferably 3-4. Most preferably, y is 3.

As used herein, the value of z denotes an alkyl chain of —CH$_2$— groups connected between —N$^+$(R$_3$)(R$_4$)— and —SO$_3^-$ groups of the surfactant of formula (I). In one or more embodiments, z is an integer selected from 3 and 4. In a preferred embodiment, z is 3.

Surfactant structures containing ethylene oxide (EO) units may show increased water solubility, as well as low interfacial tension (IFT) and low viscosity microemulsion in the absence of a co-solvent such as methanol [Negin, C., S. Ali, and Q. Xie, *Most common surfactants employed in chemical enhanced oil recovery*. Petroleum, 2017. 3(2): p. 197-211, incorporated herein by reference in its entirety]. Low IFT values may be obtained even in harsh reservoir conditions by including EO units to the chemical structure of a surfactant. The hydrogen bonding between ether oxygen of EO units and water molecules promotes the surfactant to adsorb at the interface between aqueous and oil, which leads to reduced IFT and increased solubility [Levitt, D., et al. *Design of an ASP flood in a high-temperature, high-salinity, low-permeability carbonate*. in *International Petroleum Technology Conference*. 2011. International Petroleum Technology Conference, incorporated herein by reference in its entirety]. It has been reported that certain properties of surfactants may be tuned by changing their degree of ethoxylation [Penfold, J., et al., *Impact of the degree of ethoxylation of the ethoxylated polysorbate nonionic surfactant on the surface self-assembly of hydrophobin-ethoxylated polysorbate surfactant mixtures*. Langmuir, 2014. 30(32): p. 9741-9751, incorporated herein by reference in its entirety]. As used herein, the value of n denotes the degree of ethoxylation (—OC$_2$H$_4$—) of the surfactant of formula (I). In one or more embodiments, n is an integer in a range of 1-15, preferably 2-14, preferably 3-13, preferably 4-12, preferably 5-11, preferably 6-10, preferably 7-9. Most preferably, n is an integer in a range of 2-10, 4-8, or 5-7. It is equally envisaged that the surfactant disclosed herein may have values for x, y, z, and/or n that fall outside of the aforementioned preferred ranges and still provide suitable surfactants of formula (I).

In one or more embodiments, the surfactant disclosed herein has a formula (II)

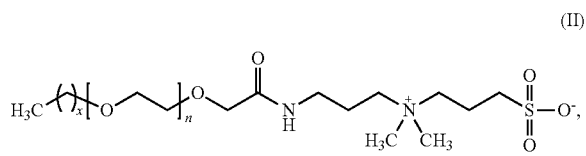

(II)

wherein n is an integer in a range of 1-15, preferably 2-14, preferably 3-13, preferably 4-12, preferably 5-11, preferably 6-10, preferably 7-9. Most preferably, n is an integer in a range of 2-10, 4-8, or 5-7. In a related embodiment, x is an integer in a range of 5-21, preferably 7-20, preferably 9-19, preferably 11-18, preferably 13-17, preferably 15-16. Most preferably, x is an integer in a range of 11-13.

In one or more embodiments, the surfactant of the present disclosure has a number average molecular weight (Mn) of 500-2,000 g/mol, preferably 600-1,900 g/mol, preferably 700-1,800 g/mol, preferably 800-1,700 g/mol, preferably 900-1,600 g/mol, preferably 1,000-1,500 g/mol, preferably 1,100-1,400 g/mol, preferably 1,200-1,300 g/mol. However, in certain embodiments, the surfactant has an average molecular weight that is less than 500 g/mol or greater than 2,000 g/mol.

Figure 5:
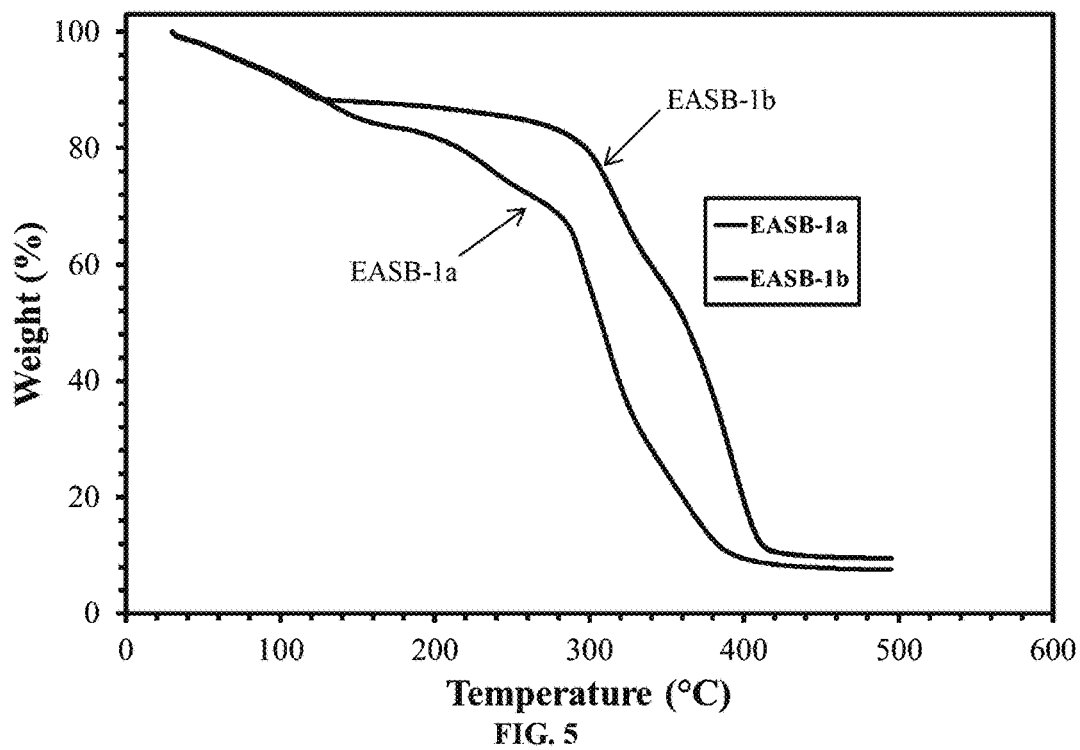
FIG. 5 is an overlay of thermal gravimetric analysis (TGA) curves of surfactants EASB-1a and EASB-1b.

The presence of sulfonate head groups in a surfactant may increase its long-term thermal stability, which is required for its applications in high-temperature reservoirs [Wang, Y., et al., *Effect of a hydrophilic head group on krafft temperature, surface activities and rheological behaviors oferucyl amidobetaines*. Journal of Surfactants and Detergents, 2014. 17(2): p. 295-301, incorporated herein by reference in its entirety]. Surfactants having sulfonate head groups may perform well in high-temperature and high-salinity environments, even in the presence of divalent ions [D'Andrea, M. G., et al., *Thermodynamic and structural characterization of zwitterionic micelles of the membrane protein solubilizing amidosulfobetaine surfactants ASB-14 and ASB-16*. Langmuir, 2011. 27(13): p. 8248-8256, incorporated herein by reference in its entirety]. The surfactant of the present disclosure exhibits good thermal stability at up to a temperature of 250-320° C., preferably 270-300 OC, more preferably 280-290° C. without degradation (see FIG. 5), which is a temperature that is 1.5-4 times, 2-3.5 times, or 2.5-3 times as the actual reservoir temperature during oil recovery processes.

In addition, amide groups [—NH—C(O)—] present in a surfactant may provide numerous advantages such as low critical micelle concentration (CMC), good water solubility, excellent biodegradability, low toxicity, and limited environmental impact [Hussain, S. S. and M. S. Kamal, *Effect of large spacer on surface activity, thermal, and rheological properties of novel amido-amine cationic gemini surfactants*. Journal of Molecular Liquids, 2017. 242: p. 1131-1137, incorporated herein by reference in its entirety]. The hydrogen bonding between carbonyl and N—H moieties may enable the surfactants to form micelle at a low CMC [Hoque, J., et al., *Aggregation properties of amide bearing cleavable gemini surfactants by small angle neutron scattering and conductivity studies*. The Journal of Physical Chemistry B, 2012. 116(32): p. 9718-9726, incorporated herein by reference in its entirety].

In one or more embodiments, the surfactant of the present disclosure is soluble in water at a temperature of 4-80° C., 10-60° C., 20-40° C., or 25-35° C. The water may be tap water, distilled water, bidistilled water, deionized water, deionized distilled water, reverse osmosis water, and/or some other water. Most preferably the water is deionized water. In one or more embodiments, the surfactant is soluble in a saline solution at a temperature of 4-80° C., 10-60° C., 20-40° C., or 25-35° C. Minerals contained in the saline solution used herein include, but are not limited to, sodium, calcium, magnesium, potassium, sulfate, chloride, bicarbonate, carbonate, bromide, and fluoride. In one embodiment, the surfactant is soluble in natural sea water or simulated sea water having sodium present at a concentration of 5-40 g/L, 10-30 g/L, or about 18 g/L, calcium present at a concentration of 0.25-2 g/L, 0.5-1.5 g/L, or about 0.7 g/L, magnesium present at a concentration of 0.5-4 g/L, 1-3 g/L, or about 2 g/L, sulfate present at a concentration of 2-8 g/L, 3-6 g/L, or about 4 g/L, chloride at a concentration of 15-60 g/L, 20-40 g/L, or about 30 g/L, and bicarbonate present at a concentration of 0.05-0.2 g/L, 0.08-0.15 g/L, or about 0.1 g/L, each relative to a total volume of the solution. In another embodiment, the surfactant is soluble in formation water or simulated formation water having sodium present at a concentration of 30-100 g/L, 50-80 g/L, or about 60 g/L, calcium present at a concentration of 8-40 g/L, 15-30 g/L, or about 20 g/L, magnesium present at a concentration of 1-5 g/L, 2-4 g/L, or about 2.5 g/L, sulfate present at a concentration of 0.1-1 g/L, 0.2-0.6 g/L, or about 0.4 g/L, chloride at a concentration of 60-200 g/L, 100-160 g/L, or about 130 g/L, and bicarbonate present at a concentration of 0.1-1 g/L, 0.2-0.5 g/L, or about 0.4 g/L, each relative to a total volume of the solution.

As used herein, critical micelle concentration (CMC) refers to the concentration of surfactants above which micelles form. The value of the CMC for a given dispersant in a given medium depends on temperature, pressure, and on the presence of other surface active substances and electrolytes. In one embodiment, the surfactant of the present disclosure has a critical micelle concentration of $1.8 \times 10^{-4}$-$3.5 \times 10^{-4}$ mol/L, $2.0 \times 10^{-4}$-$3.0 \times 10^{-4}$ mol/L, or $2.2 \times 10^{-4}$-$2.5 \times 10^{-4}$ mol/L in water at a temperature of 4-80° C., 10-60° C., 20-40° C., or 25-35° C. In one related embodiment, the surfactant has a critical micelle concentration of $1.5 \times 10^{-4}$-$3.0 \times 10^{-4}$ mol/L, $1.7 \times 10^{-4}$-$2.8 \times 10^{-4}$ mol/L, or $1.9 \times 10^{-4}$-$2.2 \times 10^{-4}$ mol/L in the aforementioned natural sea water or simulated sea water at a temperature of 4-80° C., 10-60° C., 20-40° C. or 25-35° C. In another related embodiment, the surfactant has a critical micelle concentration of $1.0 \times 10^{-4}$-$2.5 \times 10^{4}$ mol/L, $1.5 \times 10^{-4}$-$2.2 \times 10^{-4}$ mol/L, or $1.7 \times 10^{-4}$-$2.0 \times 10^{-4}$ mol/L in the aforementioned formation water or simulated formation water at a temperature of 4-80° C., 10-60° C., 20-40° C., or 25-35° C. Critical micelle concentration of the surfactant of formula (I) having an n value (i.e. degree of ethoxylation) in a range of 1-6, 2-5, or 3-4 may be at least 10%, preferably at least 15%, preferably at least 18%, preferably at least 20%, preferably at least 22%, preferably at least 25%, preferably at least 28%, preferably at least 30%, preferably at least 35%, and up to 40% less than that of a substantially similar surfactant of formula (I) having an n value in a range of 7-15, 8-12, or 9-10 at a temperature of 4-50° C., 10-40° C., 20-35° C., or 25-30° C. (See Table 2).

The surfactant of the present disclosure may be especially suitable for recovery processes of petrochemicals from reservoirs with high salinity and elevated temperature. The surfactant may be also used in formulating detergents, which can include one or more conventional additives such as buffers, abrasives, bleaching agent, brighteners, fragrances, dyes, antistatic agents, antimicrobial agents, enzymes, and the like.

According to a second aspect, the present disclosure relates to a method of synthesizing the surfactant of the first aspect. The method involves mixing a carboxylic acid of formula (III)

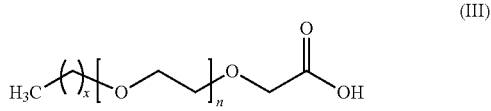
(III)

or a salt thereof, a solvate thereof, or a mixture thereof with an amine of formula (IV)

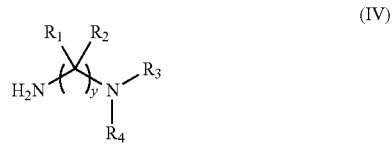
(IV)

or a salt thereof, a solvate thereof, a stereoisomer thereof, or a mixture thereof in the presence of a fluoride salt to form a mixture, heating the mixture to obtain an intermediate, and reacting the intermediate with a sultone of formula

(V)

or a salt thereof, a solvate thereof, or a mixture thereof in a solvent to form the surfactant, wherein (i) $R_1$ and $R_2$ are independently selected from the group consisting of a hydrogen, an optionally substituted alkyl, and an optionally substituted cycloalkyl, (ii) $R_3$ and $R_4$ are independently selected from the group consisting of an optionally substituted alkyl, and an optionally substituted cycloalkyl, (iii) n is an integer in a range of 1-15, (iv) x is an integer in a range of 5-21, (v) y is an integer in a range of 2-5, and (vi) z is an integer selected from 3 and 4.

In one or more embodiments, x of the carboxylic acid of formula (III) is an integer in a range of 5-21, preferably 7-20, preferably 9-19, preferably 11-18, preferably 13-17, preferably 15-16. Most preferably, x is an integer in a range of 11-13. In related embodiments, n of the carboxylic acid of formula (III) is an integer in a range of 1-15, preferably 2-14, preferably 3-13, preferably 4-12, preferably 5-11, preferably 6-10, preferably 7-9. Most preferably, n is an integer in a range of 2-10, 4-8, or 5-7. Exemplary carboxylic acids that may be used herein include, but are not limited to, glycolic acid ethoxylate lauryl ether, glycolic acid ethoxylate hexyl ether, glycolic acid ethoxylate heptyl ether, glycolic acid ethoxylate octyl ether, glycolic acid ethoxylate nonyl ether, glycolic acid ethoxylate decyl ether, glycolic acid ethoxylate tetradecyl ether, glycolic acid ethoxylate hexadecyl ether, glycolic acid ethoxylate stearyl ether, glycolic acid ethoxylate nonadecyl ether, glycolic acid ethoxylate eicosyl ether, and glycolic acid ethoxylate heneicosyl ether. In one or more embodiments, the carboxylic acid of formula (III) has a number average molecular weight of 250-900 g/mol, preferably 300-850 g/mol, preferably 350-800 g/mol, preferably 400-750 g/mol, preferably 450-700 g/mol, preferably 500-650 g/mol, preferably 550-600 g/mol. In a preferred embodiment, the carboxylic acid is glycolic acid ethoxylate lauryl ether with a number average molecular weight of about 360 g/mol. In another preferred embodiment, the carboxylic acid is glycolic acid ethoxylate lauryl ether with a number average molecular weight of about 690 g/mol.

In one or more embodiments, $R_1$ and $R_2$ of the amine of formula (IV) are independently selected from the group consisting of a hydrogen and a methyl. In a preferred embodiment, $R_1$ and $R_2$ are a hydrogen. In a related embodiment, $R_3$ and $R_4$ of the amine of formula (IV) are independently selected from the group consisting of a methyl, an ethyl, and an isopropyl. In a preferred embodiment, $R_3$ and $R_4$ are a methyl. In another related embodiment, y of the amine of formula (IV) is an integer in a range of 2-5, preferably 3-4. In a preferred embodiment, y is 3. In a most preferred embodiment, the amine of formula of (IV) is 3-(dimethylamino)-1-propylamine. Other amines that may be used in addition to or in lieu of 3-(dimethylamino)-1-propylamine include, but are not limited to, 2-(dimethylamino)ethylamine, 2-(diethylamino)ethylamine, 1-dimethylamino-2-propylamine, 3-(diethylamino)propylamine, (3-amino-2-methylpropyl)dimethylamine, (3-amino-1-methylpropyl)dimethylamine, N,N,2,2-tetramethyl-1,3-propanediamine, 4-(dimethylamino)butylamine, 5-(dimethylamino)amylamine, 5-(diethylamino)pentylamine, and 5-(diisopropylamino)amylamine.

In one or more embodiments, z of the sultone of formula (V) is an integer selected from 3 and 4. In a related embodiment, the sultone of formula (V) is selected from 1,3-propanesultone and 1,4-butanesultone. In a preferred embodiment, z is 3, and the sultone of formula (V) is 1,3-propanesultone.

The method of the present disclosure may involve an amidation reaction of the mixture comprising the carboxylic acid of formula (III) and the amine of formula (IV) to produce a corresponding intermediate of formula (VI)

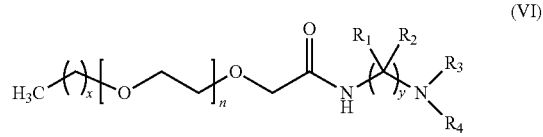
(VI)

or a salt thereof, a solvate thereof, a stereoisomer thereof, or a mixture thereof, wherein values for x and n are consistent with those described for the carboxylic acid of formula (III), and $R_1$, $R_2$, $R_3$, and $R_4$, as well as value for y are consistent with those described for the amine of formula (IV).

In a preferred embodiment, reacting the mixture comprising the carboxylic acid of formula (III) with the amine of formula (IV) is conducted in neat (solvent-free) condition. It is equally envisaged that the reaction may be adapted to be performed in a solvent such as benzene, xylene, dimethylformamide, tetrahydrofuran, ethyl acetate, diethyl ether, acetonitrile, dimethyl sulfoxide, methylene chloride, chloroform, nitrobenzene, isopropanol, and mixtures thereof. In a preferred embodiment, a molar ratio of the amine of formula (IV) to the carboxylic acid of formula (III) is in a range of 1:1 to 5:1, preferably 1:2 to 1:4, or about 2:7. In a preferred embodiment, the amine is introduced to the mixture in a two-stage or multi-stage fashion. For example, a first portion of the amine which is 50-70%, 55-65%, or about 57% of a total mole of the amine used herein may be added to the mixture and allowed to react with the carboxylic acid for 3-9 hours, 5-7 hours, or about 6 hours, and subsequently a second portion of the amine which is 30-50%, 35-45%, or about 43% of a total mole of the amine used herein may be added to the same mixture and allowed to react with the carboxylic acid for 2-8 hours, 4-6 hours, or about 5 hours. Alternatively, the amine may be introduced to the mixture in one batch and allowed to react with the carboxylic acid for 5-20 hours, 8-15 hours, or about 12 hours. In one or more embodiments, the aforementioned mixture is heated at a temperature of 50-200° C., preferably 100-190° C., preferably 120-180° C., preferably 130-170° C., preferably 140-160° C. under agitation. An external heat source, such as an oil bath, an oven, microwave, or a heating mantle, may be employed to heat the mixture. The mixture may be agitated throughout the duration of the reaction by employing a rotary shaker, a magnetic stirrer, or an overhead stirrer. In another embodiment, the mixture is left to stand (i.e. not agitated). In one embodiment, the mixture is sonicated in an ultrasonic bath or with an ultrasonic probe. The amidation reaction may be conducted in inert gas (e.g. nitrogen, argon, helium). Also, in some embodiments, the reaction may not be conducted in inert gas, but in a vacuum. In a preferred embodiment, the intermediate of formula (VI) is collected as an oil that may be separated and washed in acetone, ethyl acetate, and/or iso-propanol and then dried. In one embodiment, the oil may be dried under vacuum until a constant weight is achieved. In a preferred embodiment, the step forming the intermediate of formula (VI) has a product yield of at least 75%, preferably at least 80%, preferably at least 90%, preferably at least 92%, preferably at least 94%, preferably at least 96%, preferably at least 97%.

In one or more embodiments, the mixture comprises a fluoride salt. The fluoride salt may be present as a catalyst to accelerate the amidation reaction. In a preferred embodiment, the fluoride salt used herein is at least one selected from the group consisting of sodium fluoride, potassium fluoride, silver fluoride, cesium fluoride, and tetrabutylammonium fluoride. In a most preferred embodiment, the fluoride salt is sodium fluoride. In one or more embodiments, a molar ratio of the fluoride salt to the carboxylic acid is in the range of 1:5 to 1:20, preferably 1:6 to 1:18, preferably 1:8 to 1:15, preferably 1:9 to 1:12, or about 1:10. Other amide bond formation reagents and catalysts that may be used in addition to or in lieu of the fluoride salt include, but are not limited to, carbodiimides such as 1-ethyl-3-(3-dimethylaminopropyl)carbodiimide (EDC), N,N'-dicyclohexylcarbodiimide (DCC), 1H-benzotriazole derivatives such as 1-[bis(dimethylamino)methylene]-1H-1,2,3-triazolo[4,5-b]pyridinium 3-oxid hexafluorophosphate (HATU), O-(benzotriazol-1-yl)-1,1,3,3-tetramethyluronium hexafluorophosphate (HBTU), O-benzotriazol-1-yl-1,1,3,3-tetramethyluronium tetrafluoroborate (TBTU), as well as phosphoric acid, sulfuric acid, boric acid, silica gel, and zeolite.

In one or more embodiments, the mixture further comprises a molecular sieve. The molecular sieve may facilitate the removal of by-product water produced during the amidation reaction. Non-limiting exemplary molecular sieves applicable to the method disclosed herein include aluminosilicate minerals, porous glass, activated carbon, clay, and mesoporous silica. In a preferred embodiment, the molecular sieve comprises aluminum oxide ($Al_2O_3$). In a most preferred embodiment, the molecular sieve comprises microporous aluminum oxide having an average pore size of 0.2-0.5 nm, or 0.3-0.4 nm. Other drying agents that may be used in addition to or in lieu of the molecular sieve include, but are not limited to zeolites, anhydrous sodium sulfate, anhydrous magnesium sulfate, anhydrous calcium chloride, and anhydrous calcium sulfate. Conventional water removing apparatus such as Dean-Stark trap may be utilized in addition to the aforementioned drying agents.

The method disclosed herein also involves reacting the intermediate of formula (VI) with a sultone of formula (V), thereby producing the surfactant of the first aspect. In a preferred embodiment, reacting the intermediate with the sultone is conducted in a polar aprotic solvent, preferably in ethyl acetate. Exemplary polar aprotic solvents that may be used in addition to or in lieu of ethyl acetate include, but are not limited to, dimethylformamide, tetrahydrofuran, acetone, acetonitrile, and dimethyl sulfoxide. It is equally envisaged that the reaction may be adapted to be performed in polar protic solvent such as methanol, ethanol, n-propanol, isopropyl alcohol, n-butanol, and mixtures thereof. In certain embodiments, reacting the intermediate with the sultone is conducted without a solvent. In a preferred embodiment, the reacting is performed at a concentration of the sultone in a range of 0.01-10 M, preferably 0.05-5 M, preferably 0.1-2 M, preferably 0.15-0.5 M. In a preferred embodiment, a molar ratio of the sultone to the intermediate is in a range of 4:1 to 1:2, preferably 3:1 to 1:1, or about 3:2. In a preferred embodiment, the aforementioned reacting is conducted under agitation at a temperature of up to 120° C., preferably 50-100° C., preferably 60-95° C., preferably 70-90° C., preferably 75-85° C., or about 80° C. and has a reaction time of up to 36 hours, preferably 2-24 hours, preferably 6-16 hours, preferably 8-14 hours, or about 12 hours. In a preferred embodiment, the surfactant is collected as a viscous substance that may be separated and washed in acetone and then dried. In one embodiment, the surfactant may be dried under vacuum until a constant weight is achieved. In a preferred embodiment, the step forming the surfactant of formula (I) has a product yield of at least 70%, preferably at least 75%, preferably at least 80%, preferably at least 82%, preferably at least 84%, preferably at least 86%, preferably at least 88%, preferably at least 90%.

The examples below are intended to further illustrate protocols for preparing, characterizing the surfactants, and uses thereof, and are not intended to limit the scope of the claims.

Example 1

Materials

Glycolic acid ethoxylate lauryl ether (average $M_n$ ~360, 98%, sigma), glycolic acid ethoxylate lauryl ether (average $M_n$ ~690, sigma), 3-(dimethylamino)-1-propylamine (Aldrich, 99%), sodium fluoride (ACS reagent, ≥99%), 1,3-propanesultone (98%, Aldrich), aluminum oxide (puriss., ≥98% $Al_2O_3$ basis) were used for the synthesis of EASB-1a and EASB-1b. Solvents were distilled for the synthesis and purification of EASB-1a and EASB-1b. Salts for the preparation of formation water (FW) and sea water (SW) including $NaHCO_3$, $NaCl$, $CaCl_2$, $Na_2SO_4$, and $MgCl_2$ were purchased from Sigma-Aldrich. Table 1 summarizes the amount of each ion in FW and SW.

TABLE 1

| Composition of simulated oilfield water | | |
|---|---|---|
| Ions | Formation water (g/L) | Sea water (g/L) |
| Na | 59.5 | 18.3 |
| Ca | 19.1 | 0.7 |
| Mg | 2.5 | 2.1 |
| $SO_4^{2-}$ | 0.4 | 4.3 |

TABLE 1-continued

Composition of simulated oilfield water

| Ions | Formation water (g/L) | Sea water (g/L) |
|---|---|---|
| Cl⁻ | 132.1 | 32.2 |
| HCO₃⁻ | 0.4 | 0.1 |
| Total | 214 | 57.7 |

Example 2

Characterization Methods
(i) Structure Confirmation

Nuclear Magnetic Resonance (NMR) data was obtained on a 500 MHz Jeol 1500 spectrometer. Tetramethylsilane was used as the reference and chloroform-d was used as the solvent in all measurements. The NMR readings were noted in ppm. IR graph was obtained on a 16F model of Perkin-Elmer FTIR spectrometer, and the values were acquired in $cm^1$.

(ii) Thermogravimetric Analysis

Thermogravimetric analysis (TGA) was conducted by TA apparatus (SDT Q600 instrument) at a warming temperature of 20° C./min and a test temperature ranging from 30 to 500° C. with a constant nitrogen flow (100 mL/min).

(iii) Solubility Tests

Solubility tests were performed on 1 wt % solutions of each surfactant in FW, SW, and DW. As shown in FIGS. 1A-C and 2A-C, clear solutions indicated that the surfactants were soluble and compatible with the desired water. Solutions with poor solubility tend to precipitate and/or become milky when mixed with water.

(iv) Surface Tension Analysis

The surface tension of EASB-1a and EASB-1b was studied using an optical tensiometer (Attension Theta, Biolin Scientific). Temperatures for the measurements were set at 30° C. and 60° C., respectively. The surface tension of deionized water was measured before surface tension analysis of the sample solutions. Before the images were taken, the maximum drop possible before it falls off the needle was created and allowed to reach equilibrium. Equilibrium was determined from the live readings of surface tension measurement displayed on the tensiometer software.

At 30° C., the image of the drop was taken for ten seconds at 15 frames per second (fps). At 60° C., the images of the drop were taken for two seconds at 38 fps. The difference in the time frame was intended to minimize the effect of evaporation affecting surface tension results at 60° C. The average data point of the calculated surface tension per frame was reported as surface tension.

Other surface properties determined from surface tension were as follows: critical micelle concentration (cmc), surface tension corresponding to cmc ($\gamma_{cmc}$), surface tension lowering ($\pi_{cmc}$), maximum surface access ($r_{max}$), and minimum area per molecule ($A_{min}$). The following equations (1)-(3) were used to determine these surface properties:

$$\pi_{cmc} = \gamma_0 - \gamma_{cmc} \quad (1)$$

$$\Gamma_{max} = -\frac{1}{nRT}\left(\frac{d\gamma}{dlnC}\right)_T \quad (2)$$

$$A_{min} = 10^{18}/N_A\Gamma_{max} \quad (3)$$

where $\gamma_0$ is the surface tension of the brine (FW or SW), $N_A$ is Avogadro number, $d\gamma/dlnC$ is the slope below cmc in surface tension plot, C is the surfactant concentration in brine, T is temperature, R is the gas constant, and n=1 in case of this class of zwitterionic surfactants.

Example 3

Synthesis Overview

Betaine type zwitterionic surfactants were synthesized as depicted in FIG. 1. Unlike previously reported methods [Chu, Z. and Y. Feng, *A facile route towards the preparation of ultra-long-chain amidosulfobetaine surfactants*. Synlett, 2009. 2009(16): p. 2655-2658; and Wang, Y., et al., *Effect of a hydrophilic head group on krafft temperature, surface activities and rheological behaviors of erucyl amidobetaines*. Journal of Surfactants and Detergents, 2014. 17(2): p. 295-301, each incorporated herein by reference in their entirety], the current synthetic procedure utilizes ethoxylated carboxylic acids rather than natural ultra-long-chain fatty acids as the starting material.

Glycolic acid ethoxylate lauryl ether 3a (average Mn ~360) was condensed with 3-(dimethylamino)-1-propylamine under the catalytic amount of sodium fluoride at 160° C. to form the intermediate 2a [Hussain, S. S., M. S. Kamal, and A. S. Sultan, *Amido-amine-based cationic gemini surfactants: thermal and interfacial properties and interactions with cationic polyacrylamide*. Journal of Surfactants and Detergents, 2017. 20(1): p. 47-55, incorporated herein by reference in its entirety]. The intermediate compound was then reacted with 1,3-propanesultone to afford the desired betaine type zwitterionic surfactant EASB-1a.

Example 4

Synthesis of Intermediate (2a and 2b)

The intermediate compounds (2a and 2b) were synthesized by adopting the procedure depicted in FIG. 1 [Chu, Z. and Y. Feng, *A facile route towards the preparation of ultra-long-chain amidosulfobetaine surfactants*. Synlett, 2009. 2009(16): p. 2655-2658, incorporated herein by reference in its entirety]. The reaction between glycolic acid ethoxylate lauryl ether (3a) (average $M_n$ ~360) (10 g, 27.78 mmol) and 3-(dimethylamino)-1-propylamine (5.68 g, 55.56 mmol) in the presence of NaF (0.12 g, 2.78 mmol) was conducted in a 100 mL 3-necked round bottom (RB) flask attached to a reflux condenser. The reaction was continued for up to 6 hours in inert condition using argon at 160° C., and the water produced was absorbed by aluminum oxide. After 6 h, additional 3-(dimethylamino)-1-propylamine (4.26 g, 41.67 mmol) was introduced and experiment was continued for extra 5 hours. The remaining 3-(dimethylamino)-1-propylamine was removed, residue was treated by cold acetone and vacuumed to obtain intermediate 2a as a pale yellow thick oil.

Intermediate 2b was synthesized through a similar approach using 3b as a starting material.

Ethoxylated alkyl amidopropyl-N—N-dimethylamine (2a)

Pale yellow thick oil. ¹H-NMR (chloroform-d, 500 MHz) δ (ppm): 0.88 (t, J=6.7 Hz, CH₃), 1.15-1.35 (m, (CH₂)$_n$), 1.51-1.61 (m, CH₂), 1.69 (t, J=6.9 Hz, CH₂), 2.25 (s, (CH₃)₂), 2.37 (t, J=7.0 Hz, CH₂), 3.28-3.38 (m, CH₂), 3.47

(t, J=7.0 Hz, CH$_2$), 3.59 (m, CH$_2$), 3.59-3.72 (m, (OCH$_2$CH$_2$)$_n$), 3.98 (s, CH$_2$), 7.54 (s, NH).

Ethoxylated alkyl amidopropyl-N—N-dimethylamine (2b)

Pale yellow thick oil. $^1$H-NMR (chloroform-d, 500 MHz) δ (ppm): 0.88 (t, J=6.7 Hz, CH$_3$), 1.14-1.34 (m, (CH$_2$)$_n$), 1.52-1.62 (m, CH$_2$), 1.70 (t, J=6.9 Hz, CH$_2$), 2.23 (s, (CH$_3$)$_2$), 2.35 (t, J=7.0 Hz, CH$_2$), 3.29-3.39 (m, CH$_2$), 3.44 (t, J=7.0 Hz, CH$_2$), 3.58 (m, CH$_2$), 3.57-3.70 (m, (OCH$_2$CH$_2$)$_n$), 3.98 (s, CH$_2$), 7.58 (s, NH).

Example 5

Synthesis of ethoxylated alkyl amidosulfobetaine (EASB-1a and EASB-1b)

The intermediate 2a (10.0 g, 22.52 mmol), 1,3-propanesultone (4.12 g, 33.78 mmol), and ethyl acetate (200 mL) were added to a 500 mL 2-necked RB flask connected with a condenser. The reaction was progressed for 12 hours at 80° C. A colorless thick material was obtained, treated by cold acetone (3×50 mL), and vacuumed to yield EASB-1a.

EASB-1b was synthesized through a similar method starting from intermediate 2b.

Ethoxylated alkyl amidosulfobetaine (EASB-1a)

Colorless viscous material. $^1$H-NMR (chloroform-d, 500 MHz) δ (ppm): 0.89 (t, J=6.7 Hz, CH$_3$), 1.22-1.32 (m, (CH$_2$)n), 1.52-1.62 (m, CH$_2$), 1.92-2.02 (m, CH$_2$), 2.15-2.25 (m, CH$_2$), 2.88-2.98 (m, (CH$_2$)$_2$), 3.14 (s, (CH$_3$)$_2$), 3.31-3.41 (m, CH$_2$)$_2$), 3.41-3.51 (m, (CH$_2$)$_2$), 3.51-3.61 (m, CH$_2$), 3.62-3.72 (m, (OCH$_2$CH$_2$)$_n$), 4.03 (m, CH$_2$), 7.99 (s, NH). $^{13}$C-NMR (chloroform-d, 125 MHz) δ (ppm): 14.1, 18.5, 22.7, 23.4, 24.6, 27.9, 29.4, 29.7, 31.9, 35.7, 48.6, 50.7, 60.7, 62.1, 62.8, 69.9-71.9, 171.5. FT-IR ν (cm$^{-1}$) 3406, 2924, 2854, 1650, 1544, 1469, 1348, 1163, 1033, 730.

Ethoxylated alkyl amidosulfobetaine (EASB-1b)

Colorless viscous material. $^1$H-NMR (chloroform-d, 500 MHz) δ (ppm): 0.88 (3H, t, J=6.7 Hz), 1.20-1.30 (m, (CH$_2$)$_n$), 1.51-1.61 (m, CH$_2$), 1.96-2.06 (m, CH$_2$), 2.12-2.22 (m, CH$_2$) 2.84-2.94 (m, (CH$_2$)$_2$), 3.12 (s, (CH$_3$)$_2$), 3.30-3.40 (m, (CH$_2$)$_2$), 3.40-3.50 (m, (CH$_2$)$_2$), 3.50-3.60 (m, CH$_2$), 3.61-3.71 (m, (OCH$_2$CH$_2$)$_n$), 4.01 (m, CH$_2$), 8.03 (s, NH). $^{13}$C-NMR (chloroform-d, 125 MHz) δ (ppm): 14.1, 18.6, 22.6, 23.5, 24.7, 27.9, 29.3, 29.4, 29.6, 31.9, 35.8, 48.6, 50.8, 60.7, 62.0, 62.7, 70.0-72.0, 171.3. FT-IR ν (cm$^{-1}$) 3420, 2923, 2855, 1655, 1547, 1467, 1349, 1102, 1036, 730.

Example 6

Structure Confirmation

Figure 4:
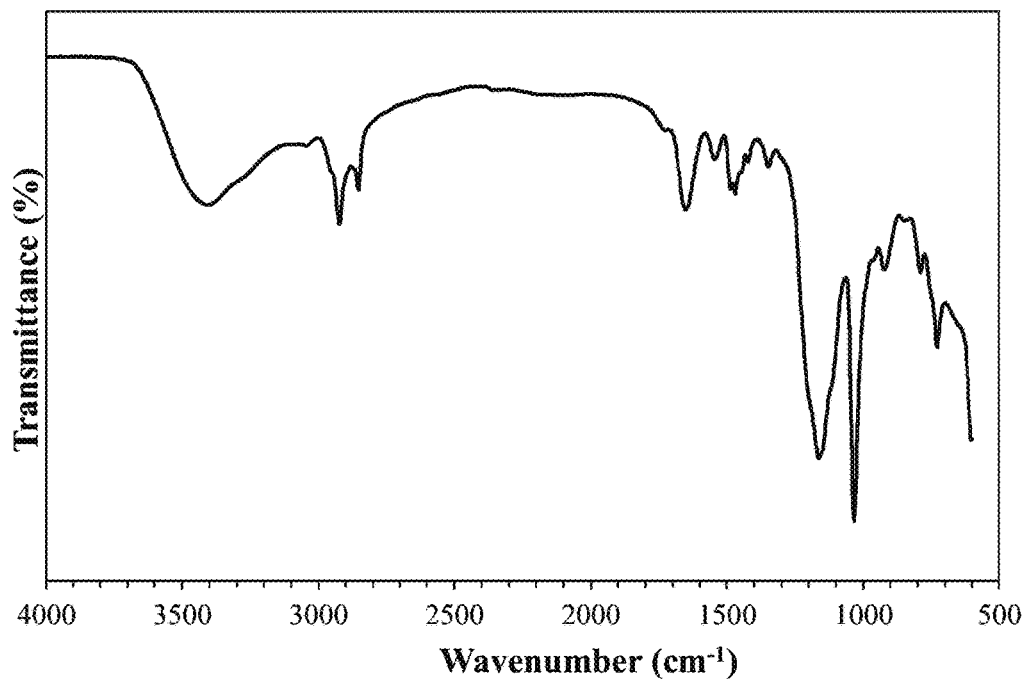

The chemical structures of all products including the intermediates were identified by NMR (1H, 13C) and FT-IR spectrophotometer. The NMR (1H, 13C) and FT-IR spectra of EASB-1a and EASB-1b were nearly identical because of similarity in their chemical structures. Therefore, as an example, the structure characterization of EASB-1a is presented. According to FT-IR data of EASB-1a (FIG. 4), a strong broad band corresponding to —OH stretching (R—C=O—OH) of the glycolic acid starting material (3a) at 3468 cm$^{-1}$ was replaced by the amide stretching (R—C=O—NH) of EASB-1a at 3406 cm$^{-1}$, and carbonyl stretching of glycolic acid starting material (R—C=O—OH) (3a) at 1736 cm$^{-1}$ was shifted towards the amide stretching (R—C=O—NH) of EASB-1a at 1650 cm$^{-1}$ [Hussain, S., et al., *Synthesis and Evaluation of Novel Amido-Amine Cationic Gemini Surfactants Containing Flexible and Rigid Spacers*. Journal of Surfactants and Detergents, 2017. 20(4): p. 777-788, incorporated herein by reference in its entirety]. Symmetric and asymmetric vibration of C—H band of the alkyl chain of EASB-1a were observed at 2854 cm$^{-1}$ and 2924 cm$^{-1}$ [Lim, J. C., et al., *Synthesis of sorbital based nonionic surfactants and characterization of interfacial and adhesive properties for waterborne pressure sensitive adhesives*. Colloids and Surfaces A: Physicochemical and Engineering Aspects, 2014. 446: p. 80-89, incorporated herein by reference in its entirety]. C—H bending was detected at 1469 cm$^{-1}$ and the ether (C—O—C) stretching vibration of EASB-1a was detected at 1163 cm$^{-1}$ [Al-Sabagh, A., et al., *Synthesis of some novel nonionic ethoxylated surfactants based on α-amino acids and investigation of their surface active properties*. Journal of Dispersion Science and Technology, 2009. 30(3): p. 427-438, incorporated herein by reference in its entirety]. In $^1$H-NMR data of EASB-1a, the peaks at around δ 0.89 and δ 1.22-1.32 indicated the presence of CH$_3$ and (CH$_2$)$_n$ in the alkyl chain [Wang, Y., et al., *Effect of a hydrophilic head group on kraft temperature, surface activities and rheological behaviors of erucyl amidobetaines*. Journal of Surfactants and Detergents, 2014. 17(2): p. 295-301, incorporated herein by reference in its entirety]. The overlapped peaks appeared at δ 3.62-3.72 could be associated with the CH$_2$ groups of EO units [Ovalles, C., et al., *Novel ethoxylated surfactants from low-value refinery feedstocks*. Fuel, 2001. 80(4): p. 575-582, incorporated herein by reference in its entirety]. The singlet peak of 6 protons at δ 3.14 could be assigned to the methyl moieties connected with the nitrogen group (R—N—(CH$_3$)$_2$—). The broad singlet peak of 1 proton at δ 7.99 could be designated to the amide N—H. In $^{13}$C-NMR data of EASB-1a, the presence of CH$_3$ and (CH$_2$)$_n$ in the alkyl chain could be confirmed by the signals at around δ 14.1 and δ 22.7-35.7, respectively. The signals at δ 50.7 could be assigned to the methyl moieties at nitrogen (—CH$_3$—N—CH$_3$—). The signals at δ 62.1 and δ 62.8 could be assigned to the CH$_2$ groups linked with the nitrogen (R—CH$_2$—N—CH$_2$—). The overlapped peaks appeared at around δ 69.9-71.9 could be assigned to the CH$_2$ groups of the EO units [Bodin, A., et al., *Structure elucidation, synthesis, and contact allergenic activity of a major hydroperoxide formed at autoxidation of the ethoxylated surfactant C12E5*. Chemical research in toxicology, 2003. 16(5): p. 575-582, incorporated herein by reference in its entirety]. The signal at δ 171.5 could be assigned to the amide carbonyl (R—C=O—NH). In general, the NMR and FT-IR data of the EASB-1a was in agreement with the chemical structure.

Example 7

Solubility Tests

It is well known that good solubility and high salt tolerance of a surfactant are the prerequisite for its oilfield applications. Using a surfactant with poor solubility in injected water (usually sea water) and reservoir brine (formation water) leads to the rejection of surfactant without further evaluation.

Surfactants bearing large hydrocarbon tail (≥C18) exhibit poor solubility in water and therefore are not suitable for oilfield applications [Kamal, M. S., S. M. Shakil Hussain, and L. T. Fogang, *A Zwitterionic Surfactant Bearing Unsaturated Tail for Enhanced Oil Recovery in High-Temperature High-Salinity Reservoirs*. Journal of Surfactants and Detergents, 2018; and Hussain, S. S., et al., *Synthesis, characterization and surface properties of amidosulfobetaine surfactants bearing odd-number hydrophobic tail*. Journal of Surfactants and Detergents, 2016. 19(2): p. 413-420, each incorporated herein by reference in their entirety]. Due to such solubility issues, most of the studies have been limited to shorter hydrocarbon tails (<C18) [Wang, Y., et al., *Effect of a hydrophilic head group on kraft temperature, surface activities and rheological behaviors of erucyl amidobetaines*. Journal of Surfactants and Detergents, 2014. 17(2): p. 295-301, incorporated herein by reference in its entirety]. However, the synthesized surfactants (EASB-1a and EASB-1b) exhibited excellent solubility in FW, SW, and DW. As depicted in FIGS. 2A-C and 3A-C, clear solutions of each surfactant in FW, SW, and DW were obtained without any observation of precipitation or phase separation.

Example 8

Thermal Degradation Behaviors

The thermal stability of the surfactant plays an important role in its application as oilfield material. The applied surfactant resides in the reservoir for long time and the reservoir temperature may cause degradation of the surfactant. Therefore, thermal stabilities of EASB-1a and EASB-1b were analyzed. The TGA thermogram of EASB-1a (FIG. 5) exhibited an initial 33% weight loss due to presence of residual water and solvents. A majority loss in weight was observed after 280° C. Similarly, EASB-1b showed an initial weight loss of about 11% due to presence of residual water and solvents. The major loss in weight was observed after 290° C. Overall, both surfactants exhibited a degradation temperature that is higher than actual reservoir conditions (≥90° C.). In addition, EASB-1b was found to be more thermally stable than EASB-1a. This indicates that the surfactant having a higher molecular weight may possess a higher degradation temperature [Lee, D. I., et al., *Synthesis and characterization of TRITON™ X-based surfactants with carboxylic or amino groups in the oxyethylene chain end*. Journal of applied polymer science, 2007. 104(1): p. 162-170, incorporated herein by reference in its entirety].

Example 9

Effect of Degree of Ethoxylation on Cmc Values

FIGS. 6-9 show the surface tension data of EASB-1a and EASB-1b in different types of brine at 30° C. and 60° C., respectively. The surface tension was observed to decrease as the concentration of the surfactant increased till a critical concentration called critical micelle concentration (cmc) was reached. There was almost no change in the surface tension at concentrations higher than cmc. The effect of EO units, temperature, and salinity on cmc, $\gamma_{cmc}$, and other surface properties were investigated.

Figure 6:
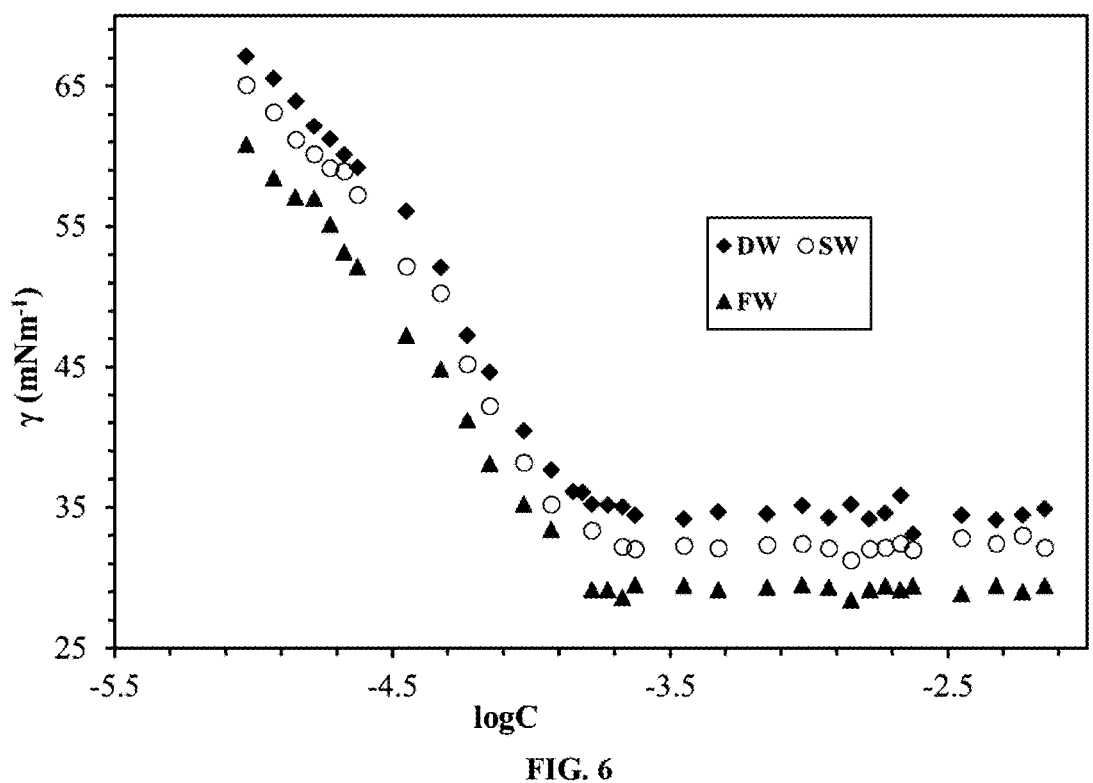
FIG. 6 is an overlay of surface tension of surfactant EASB-1a at different log of concentration measured at 30° C. in DW, SW, and FW, respectively.
Figure 7:
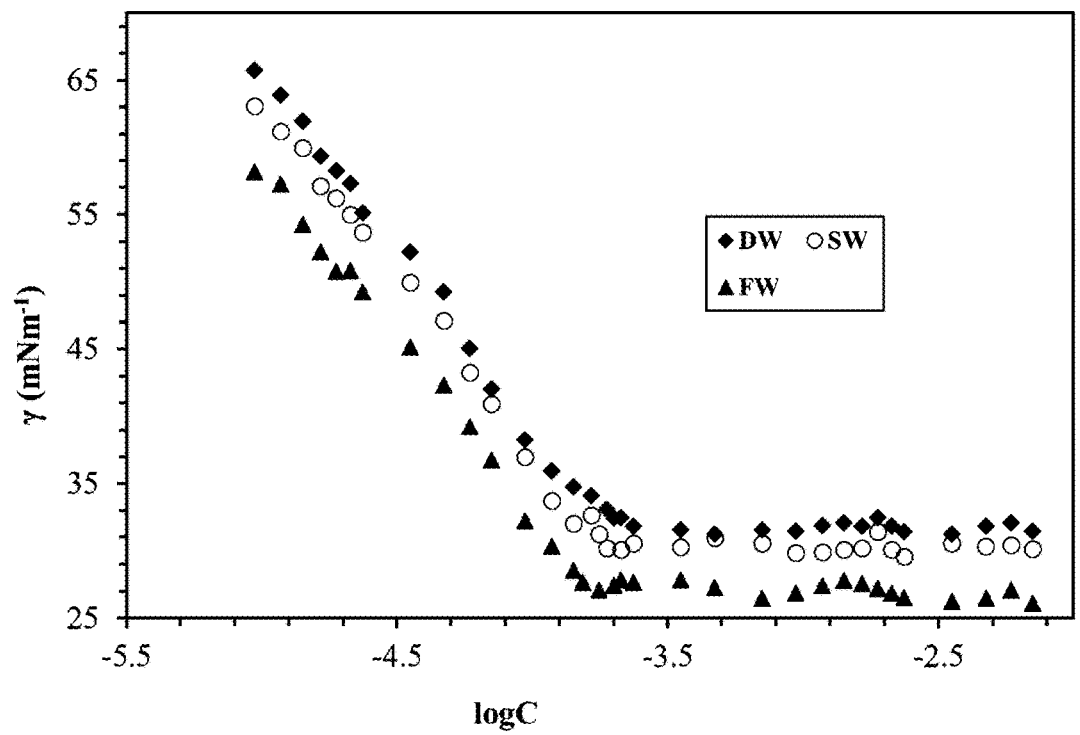
FIG. 7 is an overlay of surface tension of surfactant EASB-1a at different log of concentration measured at 60° C. in DW, SW, and FW, respectively.

The effect of salts on the surface properties was studied using FW, SW, and DW. FIG. 6 illustrates the surface tension data of EASB-1a in FW, SW, and DW at 30° C. The surface tension was seen to decrease by increasing the salinity of the water. And the lowest surface tension was observed when the surfactant was dissolved in FW. A similar change in the surface tension of the EASB-1a was also observed at 60° C. (FIG. 7). Other surface properties of EASB-1a and EASB-1b are given in Table 2.

TABLE 2

Surface properties of the surfactants

| Surfactant | Brine | T (° C.) | cmc (mol L$^{-1}$) | $\gamma_{cmc}$ (mN m$^{-1}$) | $\Gamma_{max} \times 10^6$ (mol m$^{-2}$) | $A_{min}$ (nm$^2$) |
|---|---|---|---|---|---|---|
| EASB-1a | DW | 30 | 2.35 × 10$^{-4}$ | 34.45 | 4.72 | 0.35 |
| EASB-1a | SW | 30 | 2.12 × 10$^{-4}$ | 32.23 | 4.63 | 0.36 |
| EASB-1a | FW | 30 | 1.65 × 10$^{-4}$ | 29.14 | 4.49 | 0.37 |
| EASB-1a | DW | 60 | 2.00 × 10$^{-4}$ | 32.45 | 4.15 | 0.39 |
| EASB-1a | SW | 60 | 1.88 × 10$^{-4}$ | 30.23 | 4.13 | 0.40 |
| EASB-1a | FW | 60 | 1.53 × 10$^{-4}$ | 27.65 | 4.07 | 0.41 |
| EASB-1b | DW | 30 | 3.29 × 10$^{-4}$ | 36.52 | 3.44 | 0.48 |
| EASB-1b | SW | 30 | 2.74 × 10$^{-4}$ | 34.15 | 3.35 | 0.49 |
| EASB-1b | FW | 30 | 2.20 × 10$^{-4}$ | 32.15 | 3.33 | 0.50 |
| EASB-1b | DW | 60 | 2.20 × 10$^{-4}$ | 35.25 | 3.14 | 0.53 |
| EASB-1b | SW | 60 | 1.65 × 10$^{-4}$ | 33.55 | 3.20 | 0.52 |
| EASB-1b | FW | 60 | 1.10 × 10$^{-4}$ | 29.26 | 3.20 | 0.52 |

The cmc of EASB-1a was shown to decrease by increasing the salinity of the surfactant. The surface tension corresponding to cmc ($\gamma_{cmc}$) also decreased with increasing salinity. The reduction in the cmc of a surfactant with increasing salinity may be associated with the salting out effect. The surface tension reduction is directly proportional to the amount of surfactant adsorbed at the interface. The addition of salts could reduce the repulsion between the surfactant head group that could result in closer packing at the interface. In the presence of salts, hydration of polar (head) group decreases which enhances the tendency of polar groups to adsorb at the interface. The interface between aqueous and air layers is always populated with surfactant molecules. The relative amount of the surfactant in the bulk and interface defines surface properties. Minimum area per molecule ($A_{min}$) is a significant surface property that needs to be considered as well [Feng, Y. and Z. Chu, *Correlating surface activity with structural and environmental parameters for alkylamidosulfobetaine surfactants*. Colloid and Polymer Science, 2016. 294(6): p. 957-963, incorporated herein by reference in its entirety]. Addition of salts slightly decreases the maximum surface access and increases the area per adsorbed molecule.

FIG. 7 shows the surface tension of the EASB-1a in different types of brine at 60° C. At the higher temperature, a similar reduction in the surface tension, cmc and $\gamma_{cmc}$ was observed by increasing the salinity. By comparing the data at low and high temperatures, it was noted that cmc and $\gamma_{cmc}$ was decreased with increasing temperature for all types of brine water. The change in cmc by changing temperature depends on the relative amount of two opposing effects. Increasing temperature can lower the water hydration around hydrophilic head groups which can promote micellization. However, a high temperature may also destroy the structured water around the hydrophobic tail that can reduce the micellization [Shaban, S. M., I. Aiad, and A. R. Ismail, *Surface parameters and biological activity of N-(3-(dimethyl benzyl ammonio) propyl) alkanamide chloride cationic surfactants*. Journal of Surfactants and Detergents, 2016. 19(3): p. 501-510; and Aiad, I., et al., *Surface properties, thermodynamic aspects and antimicrobial activity of some novel iminium surfactants*. Journal of Surfactants and Detergents, 2012. 15(3): p. 359-366, each incorporated herein by reference in their entirety]. The reduction in the surface tension values by increasing temperature is associated with the decreasing hydrophilicity of the surfactant at high temperatures. The surfactant molecules become less hydrophilic at high temperatures due to the breaking of hydrogen bondings between water molecules and EO units of EASB-1a. The increase in temperature causes a reduction in the hydration of surfactant hydrophilic head group. The reduced hydration of hydrophilic group promotes the micellization. As a result, the surfactant molecules are separated from the aqueous phase and adsorbed at the interface, thus forming micelle which leads to a reduction of the surface tension. At a high temperature, surfactant molecules can form micelle at low concentration as more molecules are available due to breakage of hydrogen bond [Sayed, G. H., et al., *Synthesis, surface, thermodynamic properties of some biodegradable vanillin-modified polyoxyethylene surfactants.* Journal of Surfactants and Detergents, 2012. 15(6): p. 735-743; and Chen, L.-J., et al., *Temperature dependence of critical micelle concentration of polyoxyethylenated nonionic surfactants. Colloids and Surfaces A: Physicochemical and Engineering Aspects,* 1998. 135(1-3): p. 175-181, each incorporated herein by reference in their entirety]. The maximum surface access of the surfactant decreased with temperature for surfactants (EASB-1a and EASB-1b) increases.

Figure 8:
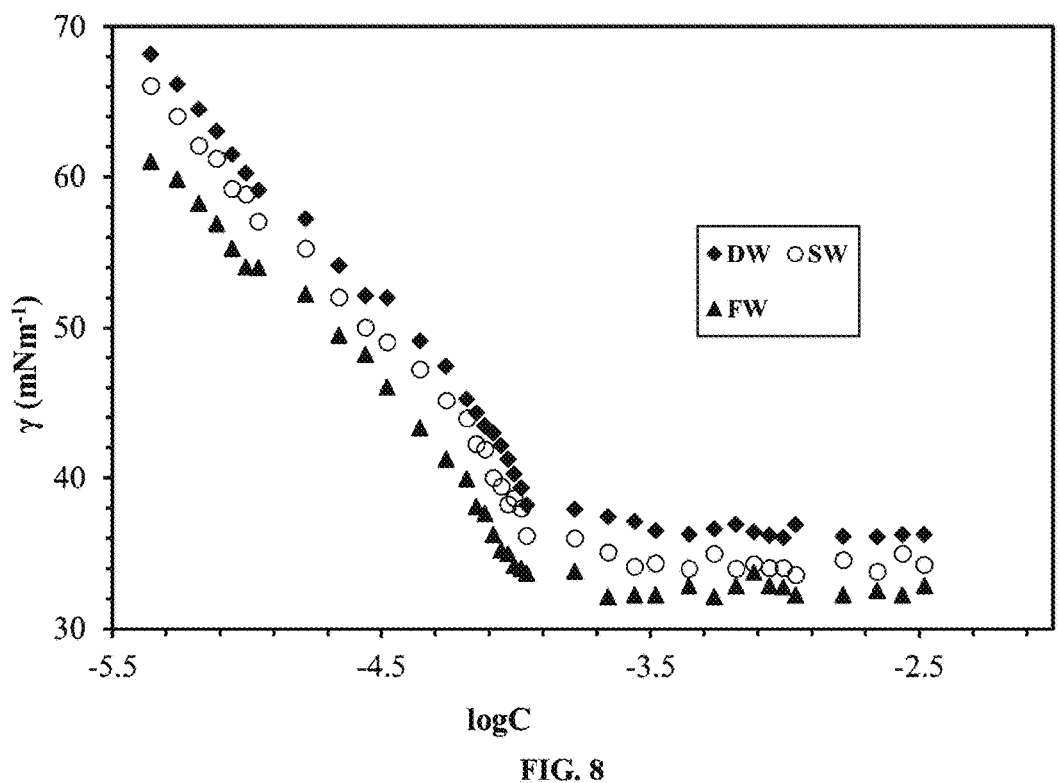
FIG. 8 is an overlay of surface tension of surfactant EASB-1b at different log of concentration measured at 30° C. in DW, SW, and FW, respectively.
Figure 9:
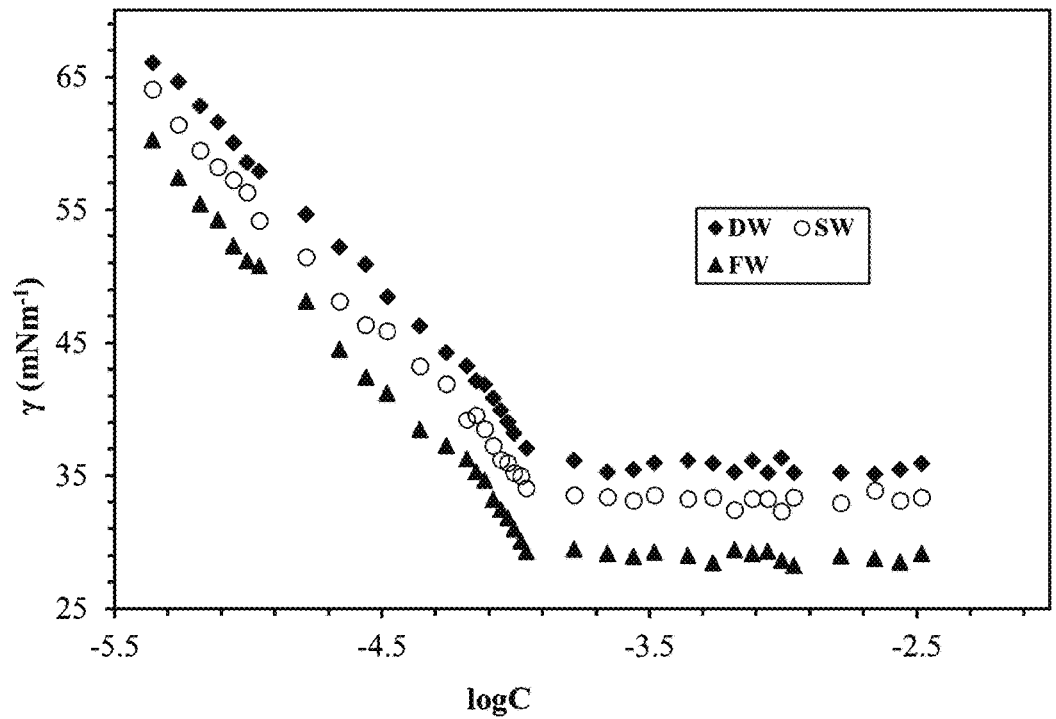
FIG. 9 is an overlay of surface tension of surfactant EASB-1b at different log of concentration measured at 60° C. in DW, SW, and FW, respectively.

FIGS. 7 and 8 show the surface tension of EASB-1b at 30° C. and 60° C., respectively. The surface tension, cmc, and $\gamma_{cmc}$ show a similar trend compared to the EASB-1a, i.e. cmc and $\gamma_{cmc}$ decrease with salinity and temperature increase. However, the cmc and $\gamma_{cmc}$ of EASB-1b are moderately higher compared to EASB-1a at all investigated temperatures and salinities. EASB-1b contains more EO units compared to EASB-1a. Increase in the number of EO units in the surfactant enhances hydrophilic character of the surfactant and improves its water solubility. Such improvements in the solubility reduce the micelle formation tendency of the surfactant which results in higher cmc with the addition of more EO units [Sayed, G. H., et al., *Synthesis, surface, thermodynamic properties of some biodegradable vanillin-modified polyoxyethylene surfactants.* Journal of Surfactants and Detergents, 2012. 15(6): p. 735-743; and Al-Sabagh, A., *Surface activity and thermodynamic properties of water-soluble polyester surfactants based on 1, 3-dicarboxymethoxybenzene used for enhanced oil recovery.* Polymers for Advanced Technologies, 2000. 11(1): p. 48-56, each incorporated herein by reference in their entirety]. The reduction in the $\gamma_{cmc}$ and cmc with the increase in the number of EO units was evident at all temperatures and salinities. The maximum surface access was reduced by enhancing the number of EO units whereas minimum area per molecules was enhanced by enhancing the number of EO units.

Example 10

Ethoxylated zwitterionic surfactants are of great interest because of advantages over organic surfactants such as excellent oilfield water solubility, high thermal stability, as well as low cmc values. The synthesis method, and thermal and surface properties of two novel ethoxylated betaine type zwitterionic surfactants (EASB-1a and EASB-1b) containing different degree of ethoxylation were studied. Solubility tests have confirmed excellent solubility of the synthesized surfactants in FW, SW, and DW. According to TGA thermogram, EASB-1a and EASB-1b demonstrate excellent thermal stabilities and the thermal degradation temperatures were in the order of: EASB-1a (280° C.)<EASB-1b (290° C.), which are greater than actual reservoir temperature (≥90° C.). The cmc and $\gamma_{cmc}$ of the EASB-1a and EASB-1b decreased by increasing the salinity of the water, and the lowest cmc and $\gamma_{cmc}$ were observed in FW. A similar reduction in cmc and $\gamma_{cmc}$ of EASB-1a and EASB-1b was also observed by increasing the temperature for all types of water tested. However, the cmc and $\gamma_{cmc}$ of EASB-1b are moderately higher compared to EASB-1a at all investigated temperatures and salinities. These betaine type zwitterionic surfactants with different degrees of ethoxylation exhibit unique properties including salt tolerance, high heat stabilities, and excellent surface properties, which may lead to their application in high salinity and high temperature reservoirs.

The invention claimed is:

1. A surfactant of formula (I)

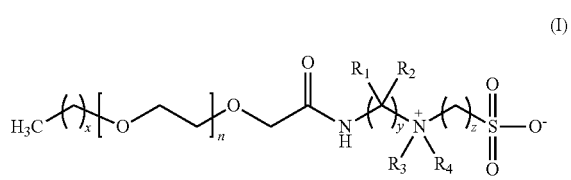

(I)

or a tautomer thereof, or a stereoisomer thereof;
wherein:
$R_1$ and $R_2$ are independently selected from the group consisting of a hydrogen, an optionally substituted alkyl, and an optionally substituted cycloalkyl;
$R_3$ and $R_4$ are independently selected from the group consisting of an optionally substituted alkyl, and an optionally substituted cycloalkyl;
n is an integer in a range of 1-15;
x is an integer in a range of 5-21;
y is an integer in a range of 2-5; and
z is an integer selected from 3 and 4.

2. The surfactant of claim 1, wherein $R_1$ and $R_2$ are independently selected from the group consisting of a hydrogen and a methyl.

3. The surfactant of claim 1, wherein $R_1$ and $R_2$ are a hydrogen.

4. The surfactant of claim 1, wherein $R_3$ and $R_4$ are independently selected from the group consisting of a methyl, an ethyl, and an isopropyl.

5. The surfactant of claim 1, wherein $R_3$ and $R_4$ are a methyl.

6. The surfactant of claim 1, wherein n is an integer in a range of 2-10.

7. The surfactant of claim 1, wherein x is an integer in a range of 11-13.

8. The surfactant of claim 1, wherein y is 3.

9. The surfactant of claim 1, which has a formula (II)

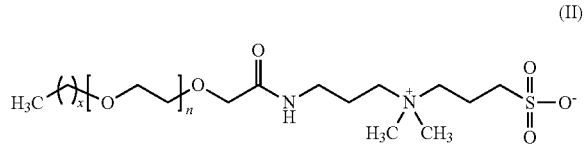

(II)

wherein:
n is an integer in a range of 1-15; and
x is an integer in a range of 11-13.

10. The surfactant of claim 1, which has a number average molecular weight of 500-1,500 g/mol.

11. A method of synthesizing the surfactant of claim 1, the method comprising:

mixing a carboxylic acid of formula (III)

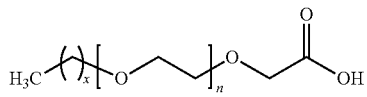
(III)

or a salt thereof with an amine of formula (IV)

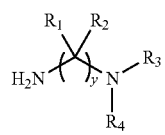
(IV)

or a salt thereof, or a stereoisomer thereof in the presence of a fluoride salt to form a mixture;
heating the mixture to obtain an intermediate; and
reacting the intermediate with a sultone of formula (V)

(V)

or a salt thereof in a solvent to form the surfactant, wherein:
$R_1$ and $R_2$ are independently selected from the group consisting of a hydrogen, an optionally substituted alkyl, and an optionally substituted cycloalkyl;
$R_3$ and $R_4$ are independently selected from the group consisting of an optionally substituted alkyl, and an optionally substituted cycloalkyl;
n is an integer in a range of 1-15;
x is an integer in a range of 5-21;
y is an integer in a range of 2-5; and
z is an integer selected from 3 and 4.

12. The method of claim 11, wherein the carboxylic acid of formula (III) has a number average molecular weight of 300-800 g/mol.

13. The method of claim 11, wherein the amine of formula of (IV) is 3-(dimethylamino)-1-propylamine.

14. The method of claim 11, wherein the sultone of formula (V) is 1,3-propanesultone.

15. The method of claim 11, wherein a molar ratio of the amine of formula (IV) to the carboxylic acid of formula (III) is in a range of 1:1 to 5:1.

16. The method of claim 11, wherein the mixture further comprises a molecular sieve.

17. The method of claim 16, wherein the molecular sieve comprises aluminum oxide.

18. The method of claim 11, wherein the fluoride salt is sodium fluoride.

19. The method of claim 11, wherein the mixture is heated at a temperature of 100-200° C.

20. The method of claim 11, wherein the reacting is conducted at a temperature of 50-100° C.

* * * * *